United States Patent [19]
Kuzuhara et al.

[11] Patent Number: 5,151,023
[45] Date of Patent: Sep. 29, 1992

[54] HEPATITIS A,B-COMBINED ADJUVANTED VACCINE

[75] Inventors: Syoji Kuzuhara, Houtaku; Koichi Odo, Kumamoto; Kyosuke Mizuno, Kumamoto, all of Japan

[73] Assignee: Juridical Foundation The Chemo-Sero-Therapeutic Research Institute, Japan

[21] Appl. No.: 344,911

[22] Filed: Apr. 27, 1989

[30] Foreign Application Priority Data

Apr. 28, 1988 [JP] Japan .................. 63-106748

[51] Int. Cl.$^5$ .................. A61K 39/12; C12N 7/00
[52] U.S. Cl. .................. 424/89; 424/88; 435/172.1; 435/172.3; 435/235.1; 435/236; 435/237; 435/239; 435/240.1
[58] Field of Search .................. 424/89, 88; 435/172.1, 435/172.3, 235.1, 236, 237, 239, 240.1

[56] References Cited

U.S. PATENT DOCUMENTS

| | | | |
|---|---|---|---|
| 4,620,978 | 11/1986 | Deamer et al. | 424/89 |
| 4,657,761 | 4/1987 | Pinto | 424/89 |
| 4,710,378 | 12/1987 | Ohtomo et al. | 424/89 |
| 4,741,901 | 5/1988 | Levinson et al. | 424/89 |
| 4,783,407 | 11/1988 | Provost et al. | 435/235.1 |
| 4,788,056 | 11/1988 | Lütticken et al. | 424/89 |

FOREIGN PATENT DOCUMENTS

| | | |
|---|---|---|
| 0156242 | 10/1985 | European Pat. Off. . |
| WO86/01826 | 3/1990 | World Int. Prop. O. . |

OTHER PUBLICATIONS

Flehmig et al., *The Journal of Infectious Diseases*, vol. 161(5) pp. 865–868, 1990.
Mazert et al., *Dev. Biol. Stand*, vol. 54, pp. 53–62, 1983.
Yvonnet et, *Develop. Biol. Stand*, vol. 65, pp. 205–207, 1986.
Coursaget et al, *Develop. Biol. Standard*, vol. 65, pp. 169–175, 1986.
Coursaget et al, *Infection and Immunity*, vol. 51, No. 3, pp. 784–787, Mar. 1986.
Sanchez et al, *Infection and Immunity*, vol. 30, No. 3, pp. 728–733, Dec. 1980.
M. E. Jolivet et al., "Induction of Biologically Active Antibodies by a Polyvalent Synthetic Vaccine Constructed without Carrier", *Infection and Immunity* 55:1498–1502, 1987.

*Primary Examiner*—Johnnie R. Brown
*Assistant Examiner*—Abdel A. Mohamed
*Attorney, Agent, or Firm*—Seed and Berry

[57] ABSTRACT

A hepatitis A, B-combined adjuvanted vaccine is disclosed in this application, said vaccine comprising an inactivated hepatitis A virus antigen, a hepatitis B virus surface antigen and an adjuvant. The present vaccine is obtained by causing the antigens to be adsorbed to the adjuvant. According to the present invention, the infection associated with hepatitis A virus and with hepatitis B virus can be prevented without causing any interference due to the mixing of these antigens and any severe side-effects, and the anti-hepatitis A virus antibody titer is greatly enhanced by the mixing.

10 Claims, No Drawings

HEPATITIS A,B-COMBINED ADJUVANTED VACCINE

FIELD OF THE INVENTION

The present invention relates to a hepatitis A,B-combined adjuvanted vaccine and, particularly, to a hepatitis A,B-combined adjuvanted vaccine comprising an inactivated hepatitis A virus (hereunder referred to as "HAV") antigen and a purified hepatitis B surface antigen (hereunder referred to as "HBs antigen") or an inactivated purified HBs antigen, which are adsorbed on aluminum gel, the inactivated HAV antigen being obtained by proliferating HAV, which has been isolated from the stool of a patient suffering from hepatitis A and which has been adapted to grow in Green monkey kidney cells, on a large scale according to cell culture technique, and then isolating and purifying it from the infected cells; the purified HBs antigen being produced by a recombinant (yeast), to which producibility of HBs antigen is imparted in accordance with a genetic recombination technique; and the inactivated purified HBs antigen being derived from the plasma of hepatitis B virus carriers (hereunder referred to as "carrier").

BACKGROUND OF THE INVENTION

Hepatitis A is a disease which sporadically breaks out through oral infection with HAV. However, recent reports on its large-scale epidemic have become rare in advanced countries, because in those countries hygienic environment has been improved as a whole. Nevertheless, there is a report stating that 1 to 1.5% of patients suffering from acute hepatitis A become fluminant and, therefore, hepatitis A is believed to be a disease worth notice, epidemiologically and clinically.

Recently, the number of people having anti-HAV antibody has been reduced year by year as the number of the reports on the epidemic has been reduced. As a result, most of people not more than 35-year-old are negative in anti-HAV antibody in the advanced countries. However, there become conspicuous, cases where such antibody-negative young people take passage to regions highly infected with indigenous hepatitis A and get infected. Taking into consideration the recent tendency that many enterprises branch out into the developing countries and that chances of traveling abroad have been increased, a preventive vaccine has been required to be immediately developed. However, any of such vaccines have not yet been put into practical use.

On the other hand, hepatitis B is a disease caused by the infection with hepatitis B virus (hereunder referred to as "HBV") through blood or body fluid. Its prognosis is not good and this disease frequently shifts to chronic hepatitis, cirrhosis and even hepatocellular carcinoma. Until now, an effective means for treating hepatitis of this type has not yet been developed. Under such circumstances, a hepatitis B vaccine derived from plasma of the carriers has first been developed as a preventive means. Moreover, to overcome the difficulty in securing starting material, which is caused by the lack of the carrier plasma, there has recently been developed a technique comprising inserting a structural gene of HBs antigen, into yeast or animal cells as host cells in accordance with a genetic recombination technique to cause the expression, producing a large amount of only HBs antigen as a source material for vaccines for preventing the hepatitis, and purifying it to obtain highly purified antigen.

It is believed that the number of hepatitis B carriers is about two hundred million in the world and that in the HAV indigenous regions such as Southeast Asia and Africa, the number of carriers almost reaches 10 to 15% of their population. This clearly shows highly latent possibility of HBV infection in the HAV indigenous regions. Therefore, in such regions, a means for preventing infection associated with hepatitis A virus and with hepatitis B virus has been eagerly requested to be developed.

Recently, there have been actively conducted many attempts for developing vaccines capable of preventing a plurality of objective diseases through only one inoculation, i.e., polyvalent vaccines (combined vaccines) for the purposes of decreasing the number of inoculations, hence decreasing accidents possibly happening during its inoculation and reducing cost in preparing vaccines, when the vaccines are produced as a means for preventing various infectious diseases. However, such mixing sometimes reduces the immunogenicities of the vaccines (interference action). Now, this becomes a major obstacle in developing a polyvalent vaccine.

SUMMARY OF THE INVENTION

Accordingly, the object of the present invention is to provide a hepatitis A,B-combined adjuvanted vaccine which resolves the problems which are encountered when the infection with both hepatitises A and B is to be prevented, and which is safe and economic.

The above object can be effectively achieved by a hepatitis A,B-combined adjuvanted vaccine comprised of an inactivated hepatitis A virus antigen, an HBs antigen and an adjuvant.

DETAILED EXPLANATION OF THE INVENTION

As a HAV usable in the present vaccine, HAV obtained by tissue culture is employed. More specifically, a large amount of HAV can be obtained by the tissue culture utilizing an HAV high-producibility cell line, i.e., GL-37 cell, which is established by cloning African Green monkey kidney cells in accordance with a colony culture technique, and also utilizing HAV KRM 003 strain which is isolated from the stool of HAV infected-patients and is highly susceptive to the GL-37 cell. HAV thus obtained is purified by a proper combination of various methods for isolating and purifying biologically active substances, such as fractionation with polyethylene glycol, ultracentrifugation, treatment with organic solvents, enzyme treatment and gel filtration, to produce a purified antigen, which is then inactivated with formalin and used in preparing the combined vaccine of the present invention.

On the other hand, the HBs antigen usable in the present invention includes those produced by a recombinant which is transformed in accordance with a genetic recombination technique to get an HBs antigen-producibility, or inactivated and purified HBs antigens derived from plasma of HBV carriers. The former antigen is produced as follows. First, a shuttle vector pAM82 is prepared, which contains the replication origins of 2μ ori plasmid, pBR322 plasmid and yeast chromosome, the leu gene of yeast, the ampicillin-resistant gene of *Escherichia coli*, and the repressive acid phosphatase promoter region of yeast. Second, the HBs gene of HBV DNA, which is isolated from HBs antigen-positive and hepatitis B e antigen-negative plasma of blood donors and then cloned, is combined with the repressive acid phosphatase promotor region of this vector, to produce a shuttle vector pAM203. Third, this vector pAM203 is inserted into a yeast cell, to obtain a transformed yeast cell. Then, the cell is cultured to cause the cell to produce the antigen. The HBs antigen produced in the yeast cell is purified according to any combination of the following methods, such as breakage of cell body, extraction from broken substances, salting out, gel filtration, ion-exchange chromatography, sucrose and cesium chloride centrifugation or the like. In this connection, the details are described in Japanese Patent Un-examined Publication (hereunder referred to as "J.P. KOKAI") Nos. 59-31799 and 60-193925.

The plasma-derived HBs antigen is prepared from HBs antigen-positive carrier plasma, as a highly purified antigen, by density-gradient centrifugation using sucrose and cesium chloride, or any combination of various ion-exchange chromatography techniques. The preparation is specifically described in Japanese Patent Publication for Opposition Purpose (hereunder referred to as "J.P. KOKOKU") No. 61-045610 filed by the inventors of this invention.

An adjuvant usable in the present invention is not critical so far as it can enhance immune activity to a desired extent and does not give any side effects. Suitably used in the present invention is aluminum gel adjuvant, in particular aluminum hydroxide gel and aluminum phosphate gel adjuvants.

One preferred embodiment of the combined vaccine of this invention is obtained by adsorbing to aluminum gel, the HAV inactivated antigen and HBs antigen prepared according to the foregoing methods. The concentration of the aluminum gel ranges from 100 to 1,000 μg/ml and preferably 400 μg/ml. The final concentrations of HAV inactivated antigen and HBs antigen are not less than 50 ng/ml and not less than 2.5 μg/ml respectively, and the mixing ratio is 1:20 to 1:200. The mixing may be performed in any manner, but preferred are the following 5 methods:

1) The HAV antigen and the HBs antigen are mixed at a desired concentration and the mixed solution is brought into contact with an adjuvant to adsorb the antigens thereon.

2) The HAV antigen is first brought into contact with an adjuvant to adsorb the HAV antigen thereon and then the HBs antigen is brought into contact with the adjuvant carrying the HAV antigen to adsorb the HBs antigen thereon.

3) The HBs antigen is first brought into contact with an adjuvant to adsorb the HBs antigen thereon and then the HAV antigen is brought into contact with the adjuvant carrying the HBs antigen to adsorb the HAV antigen thereon.

4) The HAV antigen and the HBs antigen are separately adsorbed on different adjuvants and then these adjuvants are mixed with each other.

5) An aluminum gel adjuvant is prepared in a solution containing the HAV antigen and then the HBs antigen is brought into contact with the adjuvant to adsorb the HBs antigen thereon.

The combined vaccine thus prepared is a useful pharmaceutical preparation which prevents both the infection with hepatitis A and B without any reduction in antigenic potency and any deterioration of its properties.

Moreover, this preparation never causes interference between virus antigens due to their mixing, which interference is frequently observed, in particular in case of combined vaccines for animals (such as vaccines for Newcastle disease, infectious bronchitis disease, and for akabane disease, ibaraki disease). Thus the preparation has no immune response-inhibitory effect. Moreover, the combined vaccine preparation provides higher hepatitis A immunogenicity-enhancing effect than that observed when HAV antigen is used alone.

In addition, according to the present invention, the amount of HAV antigen per unit dose can be reduced to a level lower than that required for vaccines in which no adjuvant is added, by utilizing an aluminum gel as an adjuvant. Moreover, the price of the preparation can be lowered to a level less than those comprising individual antigens, because the preparation of the present invention is polyvalent.

Efficacy and Safety of Combined Vaccine

Dr. Moritsugu et al. in National Institute of Health reported on the efficacy of a liquid type hepatitis A vaccine for marmosets, in the 33th Meeting of the Society of Japanese Virologists (1986) and in Report on Research and Development on Hepatitis A Vaccine (1985). These reports state that when the acquired antibody titer of the marmoset which is inoculated with an inactivated vaccine is not less than 1,000 mIU, the infection with a virulent virus strain of $10^3$ MID$_{50}$ can be inhibited irrespective of whether the virus enters the body of living organism through the vein or the mouth.

The inventors of this invention compared the antibody titers induced by immunization of the inactivated and purified antigens prepared by the inventors, with that of the inactivated HAV antigen (Reference) obtained from Dr. Moritsugu according to parallel line assay using a mouse. As a result, both linearity and parallelism with respect to Reference are confirmed and the relative potency is almost equal to that of Reference. Moreover, as will be described in the following Examples, it is demonstrated, by experiments using guinea pigs and mice, that when an aluminum gel was used as an adjuvant, the antibody-producibility equal to 1,000 mIU or more can be induced by immunizing these animals with HAV antigen in an amount not less than 50 ng/dose. Regarding the safety of the purified HAV antigen, a test for freedom from abnormal toxicity was conducted according to "Minimum Requirement of Biological Products" edited by Ministry of Health and Welfare of Japan and an acute toxicity test was conducted according to "Japan GLP Guide Line." Any abnormality was not observed on these animals at all.

On the other hand, the efficacy and safety of yeast-derived HBs antigens obtained according to a genetic recombination technique and those of the carrier's plasma-derived HBs antigens were already reported by the inventors of this invention in "KISO TO RINSHO (Clinical Report)," 1987, 2 1, p. 259. In this report, an yeast-derived hepatitis B vaccine containing 20 μg of HBs antigen and 400 μg of aluminum gel per 1 ml of the vaccine was subcutaneously injected into about 2200 persons three times in an amount of 0.5 ml (corresponding to 10 μg of HBs antigen) per injection for adult and 0.25 ml (corresponding to 5 μg of HBs antigen) per injection for infant, and it was found that the seroconversion rate was 94.5% for adult and 98.3% for infant. There were observed some side-effects such as local pain and itching for 11.6% of the whole subjects and malaise for 5.1% of the total subjects. However, these results are the same as those observed on the plasma-derived hepatitis B vaccine which have been put on market and whose efficacy and safety have been confirmed. Moreover, a test for freedom from abnormal toxicity was conducted on the combined vaccine according to "Minimum Requirement of Biological Products" and no abnormality was observed.

As seen from the above, it is concluded that the present combined vaccine can be sufficiently put into practical use in light of its efficacy and safety.

The present invention will be explained in more detail with reference to the following Examples and Reference Examples, and the effects practically attained by the invention will also be discussed.

REFERENCE EXAMPLE 1

Cultivation and Purification of HAV

GL-37 cells which had been derived from African Green monkey kidney cells and which had been established by and distributed from Dr. Moritsugu in Japan National Institute of Health, was repeatedly passed in a roller bottle (cultivation area=approx. 700 cm$^2$). At 19 to 23 serial passages, these cells were inoculated with HAV KRM003 strain derived from human stool, which strain had also been established by Dr. MORITSUGU so that the virus infectious dose per cell (M.O.I.) was equal to 0.1 to 1.0 and then the cells were cultivated in Eagle's minimum essential medium (E-MEM) containing 2% fetal bovine serum (hereunder referred to as "FBS") for 2 to 3 weeks. After the completion of the cultivation, the cells were washed with phosphate buffered physiological saline (hereunder referred to as "PBS"), followed by adding 10 to 15 m l per roller bottle of a lytic buffer which contained 10 mM of tris-HCl buffer of pH 7.4 (containing 1% NP 40 (available from NAKARAI CHEMICAL CO., LTD.), 0.4% sodium deoxycholate and 50 mM of EDTA); and then cultivating the cells at 37° C. for one hour in a cell roller. After harvesting them, the cell debris was removed by centrifugation at 8,000 to 10,000 rpm for 30 minutes. A five times concentrated polyethylene glycol 6,000 (available from WAKO JUNYAKU CO., LTD.) solution containing sodium chloride was added to the resultant supernatant in an amount of one volume per 4 volumes of the latter, and then the solution was stirred at 4° C. for 2 to 3 hours and was allowed to stand over night. Then, the solution was centrifuged at 8,000 to 10,000 rpm for 30 minutes and the resultant pellets were suspended in a lytic buffer. The suspension was further centrifuged at 20,000 rpm over night to pelletize the virus. The resultant virus pellets were resuspended in PBS and an equivalent volume of chloroform was added to the suspension to extract the virus at room temperature for 30 minutes. After collecting the aqueous phase (the virus phase), the residual chloroform was removed under vacuum and then the phase was treated with an enzyme. In the enzyme treatment, DNase I (available from TAKARA SHUZO CO., LTD.) and RNase A (available from Sigma Co., Ltd.), whose final concentrations were 20 to 40 μg/ml respectively, and 50 μg/ml of Proteinase K (available from Merck Co., Ltd.) were added to the aqueous phase for decomposing the protein components and nucleic acids derived from the host cells. This enzyme treatment was continued for 4 to 6 hours at 37° C. To this solution treated with the enzymes, there were added an equivalent volume of 2.5M potassium phosphate buffer (pH 7.5) and 0.8 volume of a mixed solution of ethoxyethanol and butoxyethanol (2:1 v/v), to mix the solution several times. By this organic solvent treatment, the virus was concentrated in the middle phase to form a band. The virus phase was collected, suspended in 10 mM PBS (pH 7.4) containing 0.1% Tween 80 (available from WAKO JUNYAKU CO., LTD.) and 2 mM of EDTA, and then again treated with the organic solvent. The virus suspension finally obtained was centrifuged at 10,000 rpm for 15 minutes and the resultant supernatant was passed through a gel filtration column packed with Sephacryl S 400 HR (available from Pharmacia Co., Ltd.) using PBS containing 0.002% Tween 80 as an eluent buffer. Antigen-positive fractions were collected, sterilized by filtration to obtain a purified virus solution, and then the solution was inactivated by treating it with formalin diluted by 2,000 to 4,000 time as a final concentration at 37° C. for 12 days to obtain an inactivated purified antigen solution.

REFERENCE EXAMPLE 2

Preparation of Hepatitis A,B-Combined Adjuvanted Vaccine

An aluminum gel as an adjuvant was prepared according to a method comprising addition of a 1N sodium hydroxide solution to a 10% aluminum chloride solution little by little to elevate the pH to about 7. The resulting gel was washed at least 5 times with PBS (pH 7.4) to remove free aluminum ions, and then suspended in the same buffer so as to adjust the concentration to 400 μg/ml. The aluminum gel suspension was mixed with the inactivated HAV antigen and the HBs antigen so as to adjust the final concentrations thereof to 50 to 100 ng/ml and 2.5 to 10 μg/ml, respectively. The mixed solution was stirred with a rotator at 4° C. over night to adsorb these antigens to the aluminum gel. To confirm whether or not the HAV and HBs antigens were completely adsorbed to the gel, the supernatant obtained after adsorption was subjected to a quantitative analysis, more specifically an ELISA technique for the HAV antigen and an RIA technique for the HBs antigen, but the supernatant did not show any activity of both the HAV and HBs antigens. Therefore, these antigens were considered to be completely adsorbed to the gel.

REFERENCE EXAMPLE 3

Determination of Antigen Titer and Antibody Titer

The HAV antigen titer was determined by an ELISA technique. More specifically, after coating a 96 well-microplate with anti-HAV rabbit serum as a first antibody and blocking it with bovine serum albumin (hereunder referred to as "BSA"), a specimen was reacted with the first antibody at 4° C. over night. Then, the reaction product was reacted with a second antibody, which was an anti-HAV rabbit antibody conjugated with horseradish peroxidase, at 37° C. for 2 hours and a solution of a substrate (o-phenylene-diamine) was added to let the specimen color-develop. After stopping the reaction, the absorbance at 492 nm was measured and the antigen titer was evaluated from the calibration curve of a standard material.

The anti-HAV antibody titer was determined according to a competitive inhibitory ELISA technique. More specifically, a well which had been coated with anti-HAV rabbit serum and blocked with BSA was reacted with HAV antigen at 4° C. over night (as a control, a diluent was used in place of the antigen), an antibody as a standard sample or a specimen was added thereto to cause the reaction at room temperature for 30 minutes. Then, a peroxidase-labeled anti-HAV rabbit antibody was added to cause the reaction at 37° C. for 2 hours and the solution of substrate was added to cause the specimen to color-develop. After stopping the reaction, the absorbance at 492 nm was measured and the antigen titer was calculated as a titer at which the inhibition rate was 50% based on the calibration curve of a standard material. The antibody used as the standard material was prepared so that it showed a relative titer of 2 IU/ml when the anti-HAV antibody titer of the anti-HAV Reference globulin No. 1 from Bureau of Biologics of U.S. Food and Drug Administration (F.D.A.) was set 100 IU/ml.

The titer of the HBs antigen was determined utilizing an AUSRIA II kit (available from Abbott Co., Ltd.) and based on the calibration curve of the standard material.

The titer of the anti-HBs antibody was determined by using an AUSAB kit (available from Abbott Co., Ltd.), preparing a standard sample on the basis of the WHO International Reference (IR-HBIG Lot. 26-1-77 50 IU/ml) and calculating it from the calibration curve.

EXAMPLE 1

To examine the response of the hepatitis A,B-combined adjuvanted vaccine prepared according to the same manner as in Reference Example. 4-week-old SPF guinea pigs (each group comprising 10 animals) were subcutaneously immunized with the vaccine at the back in an amount per dose shown in Table I. As a comparative test, each of hepatitis A and B vaccines was also administered.

6 weeks after the immunization, the animals were bled. The anti-HAV antibody was detected by an ELISA technique and its titer (mIU/ml) was obtained as a titer at which the competitive inhibition was 50%. In addition, the titer of the HBs antibody (mIU/ml) was determined using an AUSAB kit. Each value was expressed as a geometric means.

TABLE I

Inoculated Amount and Antibody Response of A, B and A,B-Combined Vaccines

| Vaccine | HAV-Ag (ng) | HBs-Ag (μg) | Al gel (μg) | Antibody Titer After 6 weeks (mIU/ml) |
| --- | --- | --- | --- | --- |
| A | 100 | — | 200 | 220 |
| B | — | 10 | 200 | 1870 |
| A,B-Combined | 100 | 10 | 200 | 1680 (A); 2639 (B) |

As seen from the results listed in Table I, the antibody titer of the A,B-combined vaccine was 8 times that of the hepatitis A vaccine alone in terms of the response of the anti-HAV antibody 6 weeks after the immunization, and 1.4 times that of the hepatitis B vaccine alone in terms of the response of the anti-HBs antibody 6 weeks after the immunization. No interference of the antibody responses due to the mixing of these antigens was not observed. In particular, the immunogenicity of the anti-HAV antibody was much increased due to the mixing.

EXAMPLE 2

In this example, the antibody response of the hepatitis A vaccine was investigated, when the amount of the HAV antigen was changed to 200 and 50 ng/dose while keeping unchanged the mixing ratio of the HAV antigen to the HBs antigen (Test 1) and when the amount of the HBs antigen was changed to 2.5, 5 and 10 μg/dose while keeping constant the amounts of the HAV antigen and the aluminum gel (HAV antigen: 100 ng, aluminum gel: 200 μg) (Test 2). The amount of each vaccine inoculated and the results obtained by the immunization tests are summarized in the following Tables II and III, respectively.

TABLE II

Amount of Each Vaccine Inoculated

| Vaccine | HAV-Ag (ng) | HBs-Ag (μg) | Aluminum Gel (μg) |
| --- | --- | --- | --- |
| Test 1: A alone | 200 or 50 | — | 400 (100) |
| B alone | — | 20 or 5 | 400 (100) |
| A,B-combined | 200 or 50 | 20 or 5 | 400 (100) |
| Test 2: A alone | 100 | — | 200 |
| B alone | — | 10, 5 or 2.5 | 200 |
| A,B-combined | 100 | 10, 5 or 2.5 | 200 |

TABLE III

Antibody Response and 100 mIU/ml Appearance-rate of Each Vaccine

| Vaccine | Antibody Titer (mIU/ml) | | Appearance-rate | |
| --- | --- | --- | --- | --- |
| (Test 1) | | | | |
|  | (i) | (ii) | (i) | (ii) |
| A alone | 598 | 360 | 2/5 | 0/5 |
| B alone | 5241 | 363 | — | — |
| Combined A | 1905 | 990 | 3/4 | 2/4 |
| B | 4045 | 695 | — | — |

(i): HAV-Ag 200 ng + HBs-Ag 20 μg + aluminum gel 400 μg/dose
(ii): HAV-Ag 50 ng + HBs-Ag 5 μg + aluminum gel 100 μg/dose (Test 2)

| | Anti-HAV | Anti-HBs | |
| --- | --- | --- | --- |
| A alone | 318 | — | 2/10 |
| Combined a | 743 | 1371 | 3/10 |
| b | 2270 | 1086 | 5/8 |
| c | 1190 | 809 | 4/8 | a: HAV-Ag 100 ng + HBs-Ag 10 μg + aluminum gel 200 μg/dose
b: HAV-Ag 100 ng + HBs-Ag 5 μg + aluminum gel 200 μg/dose
c: HAV-Ag 100 ng + HBs-Ag 2.5 μg + aluminum gel 200 μg/dose As seen from the results obtained by Test 1, the antibody titer of the hepatitis A vaccine was increased by mixing these two vaccines even when the amount of the HAV antigen was set 200 or 50 ng while keeping constant the mixing ratio of the HAV antigen to the HBs antigen (1:100). In addition, it was also evidenced that 1000 mIU/ml appearance-rate became also high due to the mixing of these vaccines. On the other hand, it was ensured that the titer of the HBs antibody was not adversely affected by the mixing. In Test 2, the amount of the HBs antigen was set 10, 5 and 2.5 μg while keeping unchanged the amounts of the HAV antigen and the aluminum gel, but in each of these groups, the anti-HAV antibody titer was higher than that observed when only the hepatitis A vaccine was inoculated. Moreover, there was no significant difference in 1000 mIU/ml appearance-rate when the amount of the HBs antigen was 10 μg, while the difference was significantly large for the groups wherein the HBs antigen was inoculated in an amount of 2.5 or 5 μg.

EXAMPLE 3

For the purpose of examining the influence of the aluminum gel and also the antibody responses after a first immunization with the hepatitis A,B-combined vaccine and after a booster, 5-week-old SPF guinea pigs (each group comprising 5 animals) were subcutaneously immunized with the hepatitis A,B-combined vaccine at the back in an amount per dose listed in Table IV and further immunized with the same amount of the vaccine 6 weeks after the first immunization. As a comparative test, the immunization tests with individual liquid type vaccines, an aluminum gel adjuvant vaccine and a liquid type combined vaccine were also carried out. The results obtained are summarized in Table V. The combined vaccine and the combined aluminum gel adjuvant vaccine did not indicate any significant difference from those of the individual vaccines in antibody titer both 6 weeks and 10 weeks after the immunization, and no interference was observed on the antibody response due to the mixing.

TABLE IV

Amounts of Various Antigens Inoculated

| Vaccine | HAV-Ag (ng) | HBs-Ag (µg) | Al Gel (µg) |
|---|---|---|---|
| A Liquid | 50 | — | — |
| B Liquid | — | 5 | — |
| Combined A,B Liquid | 50 | 5 | — |
| A-Al Gel | 50 | — | 100 |
| B-Al Gel | — | 5 | 100 |
| Combined A,B-Al Gel | 50 | 5 | 100 |

TABLE V

Antibody Response against Various Antigens

| Vaccine | After 6 weeks (mIU/ml) | | After 10 weeks (mIU/ml) | |
|---|---|---|---|---|
| | Anti-HAV Antibody | Anti-HBs Antibody | Anti-HAV Antibody | Anti-HBs Antibody |
| A Liquid | 170 | — | 320 | — |
| B Liquid | — | 2570 | — | 190546 |
| Combined A,B Liquid | 160 | 1698 | 460 | 112202 |
| A-Al Gel | 560 | — | 2400 | — |
| B-Al Gel | — | 14454 | — | 446684 |
| Combined A,B-Al Gel | 620 | 4571 | 2400 | 245471 |

EXAMPLE 4

The effects of the hepatitis A,B-combined vaccine of this invention were investigated on different kinds of animals. 4-week-old ddy mice (each group comprising 9 animals) were subcutaneously inoculated with the hepatitis A vaccine alone or the hepatitis A,B-combined vaccine, and then the animals were bled 6 weeks after the inoculation to determine the amount of the anti-HAV antibody and the 1000 mIU/ml appearance-rate. The results obtained are listed in Table VI below. There was not observed any interference even when the kind of the animal was changed from a guinea pig to a mouse and, as seen from the average antibody titer, and the immunogenicity of the combined vaccine was significantly increased compared with that observed when the hepatitis A vaccine was inoculated alone.

TABLE VI

Immunization Test for Mice (Anti-HAV Antibody Titer)

| Vaccine | Antibody Titer (mIU/ml) | Appearance-rate |
|---|---|---|
| A alone | 263 | 2/9 |
| Combined A,B | 889 | 4/9 |

A alone: HAV 100 ng + Al Gel 200 µg/dose
Combined A,B: HAV 100 ng + Al Gel 200 µg + HBs 10 µg/dose

EXAMPLE 5

Method for Preparing Combined A,B Vaccine

In this example, the method for preparing the combined A,B vaccine was studied with respect to the correlation between the adsorptivity of both the antigens to the aluminum gel and a kind of mixing processes and also the immonogenicity for mice. The results obtained are summarized in Table VII below.

Mixing was performed according to several ways: the process (A Alum+B) comprises first adsorbing the HAV antigen and then the HBs antigen to the aluminum gel; the process (B Alum+A) comprises adsorbing these antigens in the reverse order; the process (A Alum+B Alum) comprises separately adsorbing these antigens to the different aluminum gel and then mixing them; the process (A in B out) comprises adding a desired amount of aluminum chloride to 0.15M acetate buffer containing HAV antigen (pH 5.2) and then adjusting the pH with a 1N sodium hydroxide solution to obtain aluminum gel in which the HAV antigen was included, and thereafter adsorbing the HBs antigen to the gel; and the process (B in A out) comprises exchanging the order of using the antigens. The amount of the antigens adsorbed on the aluminum gel was determined by mixing the vaccine with a 20% phosphate-citrate solution in a ratio of 1:1 (for the HAV antigen) or mixing the vaccine with 10% phosphate-citrate solution in a ratio of 9:1 (for the HBs antigen) to dissolve the aluminum gel and then determining the amounts of the antigens according to an ELISA technique for the HAV antigen and an RIA technique for the HBs antigen. As a result, it was found that almost all of the HBs antigens as charged were adsorbed to the gel under such preparation conditions. Moreover, the amount of the HAV antigen dissolved out from the gel was as low as about 60%. However, since it was not detected in the supernatant except for some of the mixing process, it is assumed that the solutions to dissolve the aluminum gel inhibited the determination of the HAV antigen by ELISA.

In the immunological tests, the vaccines were intraperitoneally inoculated into SPF female mice of 4-week-old (ddy) (each group comprising 5 animals) and bled 6 weeks after the inoculation. The A,B-combined vaccine inoculated contained 50 ng of the HAV antigen, 5 µg of the HBs antigen and 100 µg of the aluminum gel per dose. The results are listed in Table VIII. In the mixing method composed of a combination of "in" and "out", the amount of the antigen which was not absorbed on the gel was great when the antigen was adsorbed to the gel according to the "out" method, in particular when the HAV antigen was absorbed to the gel according to the "out" method. The antibody titer of the HAV vaccine obtained by the process (B in A out) was almost the same as that of the liquid type vaccine simply composed of the HAV antigen, which supported the results in Table VIII. The mixing processes except for the process (B in A out) provided no statistically significant difference in the amount of the anti-HAV antibody from that induced by the vaccine composed of only the antigen. However, referring to calculated means of the titer, the combined vaccine obtained by the A in B out method showed high immune response compared with the vaccines obtained by the other methods.

TABLE VII

| | Adsorptibity of Antigens | | | |
| --- | --- | --- | --- | --- |
| | HAV-Ag (%) | | HBs-Ag (%) | |
| Method of Mixing | Supernatant | Gel | Supernatant | Gel |
| A Alum | 0 | 64.6 | — | — |
| A Alum + B | 0 | 67.4 | 0.2 | 99 |
| B Alum + A | 0 | 63.2 | 01 | 100 |
| A Alum + B Alum | 0 | 64.2 | 0.1 | 108 |
| A in B out | 8.8 | 53.0 | 3.6 | 82 |
| B in A out | 53.6 | 48.2 | 0.7 | 107 |

TABLE VIII

| | Immune Test of Combined Vaccine | |
| --- | --- | --- |
| Method of Mixing | Anti-HAV Antibody (mIU/ml) | Anti-HBs Antibody (mIU/ml) |
| (A alone, Liquid) | 870 | — |
| A Alum | 3090 | — |
| A Alum + B | 2340 | 523 |
| B Alum + A | 2400 | 372 |
| A Alum + B Alum | 2240 | 389 |
| A in B out | 4070 | 905 |
| B in A out | 660 | 219 |

The foregoing results, show that the hepatitis A,B-combined adjuvanted vaccine of the present invention does not induce any interference on the immune response and the immunogenicity of both HAV antigen and HBs antigen, in particular, that of the former tends to increase, so long as a unit dose of inoculation comprises not less than 50 ng of the HAV antigen and not less than 2.5 μg of the HBs antigen and so long as the combined vaccine is prepared according to the foregoing mixing processes except for the process (B in A out). These facts suggest that the preparation of this invention can be an effective polyvalent vaccine for protecting from the infection with both hepatitis virus of A and B types.

What is claimed is:

1. A hepatitis A,B-combined adjuvanted vaccine comprising an inactivated hepatitis A virus antigen, a hepatitis B virus surface antigen and an adjuvant, wherein said vaccine comprises at least 50 ng/ml of the inactivated hepatitis A virus antigen and at least 2.5 μg/ml of the hepatitis B virus surface antigen, said antigens being adsorbed from 100 to 1000 μg/ml of the adjuvant.

2. The hepatitis A,B-combined adjuvanted vaccine of claim 1 wherein said inactivated hepatitis A virus antigen is produced by cultivating hepatitis A virus-infected cells susceptive to the virus and inactivating the resultant antigen.

3. The hepatitis A,B-combined adjuvanted vaccine of claim 1 wherein the hepatitis B virus surface antigen is produced using a recombinant which has been transformed by a genetic recombination technique and which produces a hepatitis B virus surface antigen.

4. The hepatitis A,B-combined adjuvanted vaccine of claim 1 wherein the hepatitis B virus surface antigen is an inactivated purified hepatitis B virus surface antigen derived from plasma of hepatitis B virus carriers.

5. The hepatitis A,B-combined adjuvanted vaccine of claim 1 wherein the adjuvant is selected from the group consisting of aluminum hydroxide gel and aluminum phosphate gel.

6. The hepatitis A,B-combined adjuvanted vaccine of claim 1, wherein said vaccine is produced by mixing the hepatitis A virus antigen with the hepatitis B virus surface antigen, and bringing the adjuvant into contact with the mixture to cause the antigens to be adsorbed to the adjuvant.

7. The hepatitis A,B-combined adjuvanted vaccine of claim 1, wherein said vaccine is produced by bringing the adjuvant into contact with a solution containing the inactivated hepatitis A virus antigen to cause the hepatitis A virus antigen to be adsorbed to the adjuvant, and bringing the resultant adjuvant into contact with a solution containing the hepatitis B virus surface antigen to cause the hepatitis B virus surface antigen to be adsorbed to the adjuvant.

8. The hepatitis A,B-combined adjuvanted vaccine of claim 1, wherein the vaccine is produced by bringing the adjuvant into contact with a solution containing the hepatitis B virus surface antigen to cause the hepatitis B virus surface antigen to be adsorbed to the adjuvant, and bringing the resultant adjuvant into contact with a solution containing the inactivated hepatitis A virus antigen to cause the hepatitis A virus antigen to be adsorbed to the adjuvant.

9. The hepatitis A,B-combined adjuvanted vaccine of claim 1, wherein said vaccine is produced by separately bringing the adjuvant into contact with a solution containing the inactivated hepatitis A virus antigen and a solution containing the hepatitis B virus surface antigen to cause each antigen to be adsorbed to the adjuvant, and mixing the resultant adjuvants.

10. The hepatitis A,B-combined adjuvanted vaccine of claim 1, wherein said vaccine is produced by forming an aluminum gel serving as the adjuvant in a buffer solution comprising the inactivated hepatitis A virus antigen, and bringing the adjuvant into contact with the hepatitis B virus surface antigen to cause the hepatitis B virus surface antigen to be adsorbed to the adjuvant.

* * * * *